(12) United States Patent
Zarembo et al.

(10) Patent No.: US 8,239,039 B2
(45) Date of Patent: Aug. 7, 2012

(54) DEVICE ON LEAD TO PREVENT PERFORATION AND/OR FIXATE LEAD

(75) Inventors: Paul E. Zarembo, Vadnais Heights, MN (US); Yongxing Zhang, Maple Grove, MN (US); Matthew Finlay, Brooklyn Park, MN (US); Jeffrey P. Bodner, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 577 days.

(21) Appl. No.: 11/215,786

(22) Filed: Aug. 30, 2005

(65) Prior Publication Data

US 2007/0050003 A1 Mar. 1, 2007

(51) Int. Cl.
*A61N 1/05* (2006.01)
(52) U.S. Cl. ........ 607/116; 607/119; 607/122; 607/126; 607/127; 607/131
(58) Field of Classification Search .................. 607/116, 607/119, 122, 126, 127, 128, 131
See application file for complete search history.

(56) References Cited

U.S. PATENT DOCUMENTS

| | | | |
|---|---|---|---|
| 3,974,834 A * | 8/1976 | Kane | 607/127 |
| 4,217,913 A * | 8/1980 | Dutcher | 607/127 |
| 4,301,815 A | 11/1981 | Doring | |
| 4,667,686 A * | 5/1987 | Peers-Travarton | 607/127 |
| 4,924,881 A * | 5/1990 | Brewer | 607/127 |
| 4,957,118 A | 9/1990 | Erlebacher | |
| 5,545,206 A | 8/1996 | Carson | |
| 5,868,741 A | 2/1999 | Chia et al. | |
| 5,931,864 A | 8/1999 | Chastain et al. | |
| 6,161,029 A | 12/2000 | Spreigl et al. | |
| 6,185,464 B1 | 2/2001 | Bonner et al. | |
| 6,370,434 B1 * | 4/2002 | Zhang et al. | 607/122 |
| 6,697,677 B2 | 2/2004 | Dahl et al. | |
| 6,842,648 B2 | 1/2005 | Partridge et al. | |
| 2002/0147487 A1 | 10/2002 | Sundquist et al. | |
| 2003/0144718 A1 * | 7/2003 | Zeijlemaker | 607/122 |
| 2004/0230281 A1 | 11/2004 | Heil et al. | |
| 2005/0070986 A1 | 3/2005 | Tockman et al. | |
| 2007/0142890 A1 | 6/2007 | Zarembo et al. | |

FOREIGN PATENT DOCUMENTS

| | | |
|---|---|---|
| EP | 0057877 A1 | 8/1982 |
| EP | 0546414 A1 | 6/1993 |
| EP | 0779080 A1 | 6/1997 |
| GB | 2067411 | 7/1981 |
| GB | 2099307 | 12/1982 |

* cited by examiner

*Primary Examiner* — Joseph Dietrich
(74) *Attorney, Agent, or Firm* — Faegre Baker Daniels LLP

(57) ABSTRACT

This document discusses, among other things, a lead body extending longitudinally along a lead axis, a driver axially displaceable relative to the lead body, and a driven member coupled to the lead body and displaceable away from the lead axis. The driven member at least partially defines an expandable passage having at least one internal dimension. The driver is displaceable into the expandable passage and has at least one outer dimension that is larger than the at least one internal dimension of the expandable passage. An example method includes disposing a first member having a first cross-section in a lead assembly having a lead axis, an expandable passage, and a displaceable member proximate the expandable passage. The method further includes urging the first member into the expandable passage in the lead assembly, and urging the displaceable member away from the lead axis to expand the expandable passage.

38 Claims, 17 Drawing Sheets

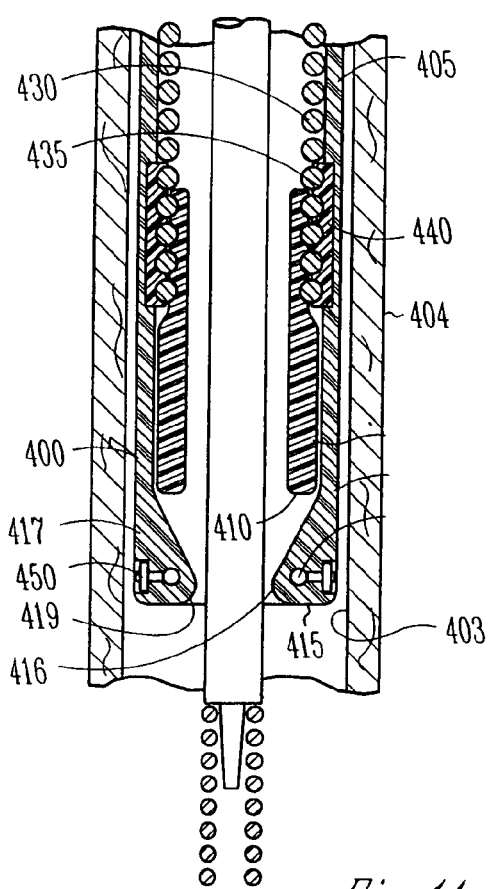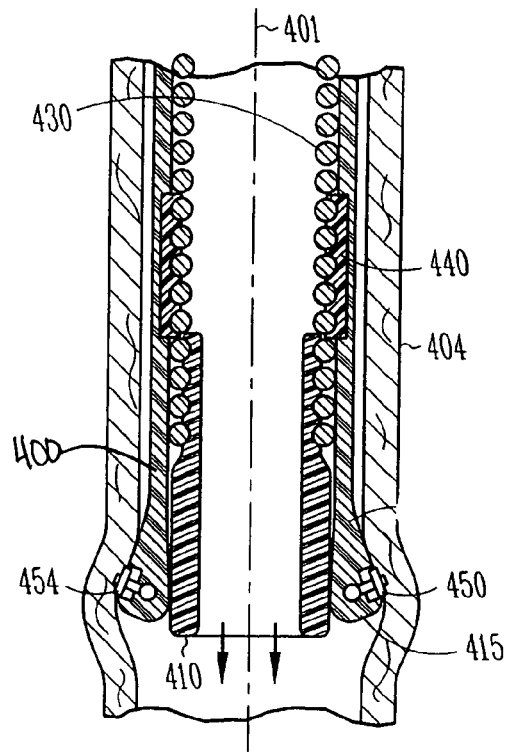
Fig. 4A  Fig. 4B
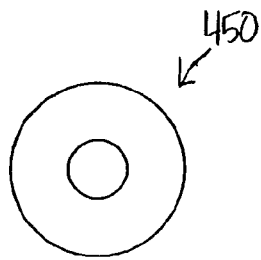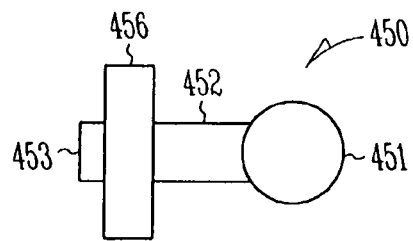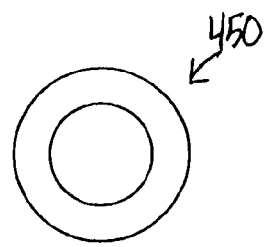
Fig. 4C  Fig. 4D  Fig. 4E

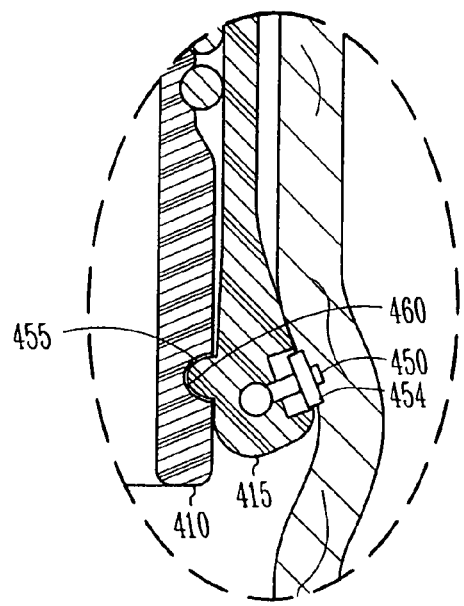
Fig. 4F
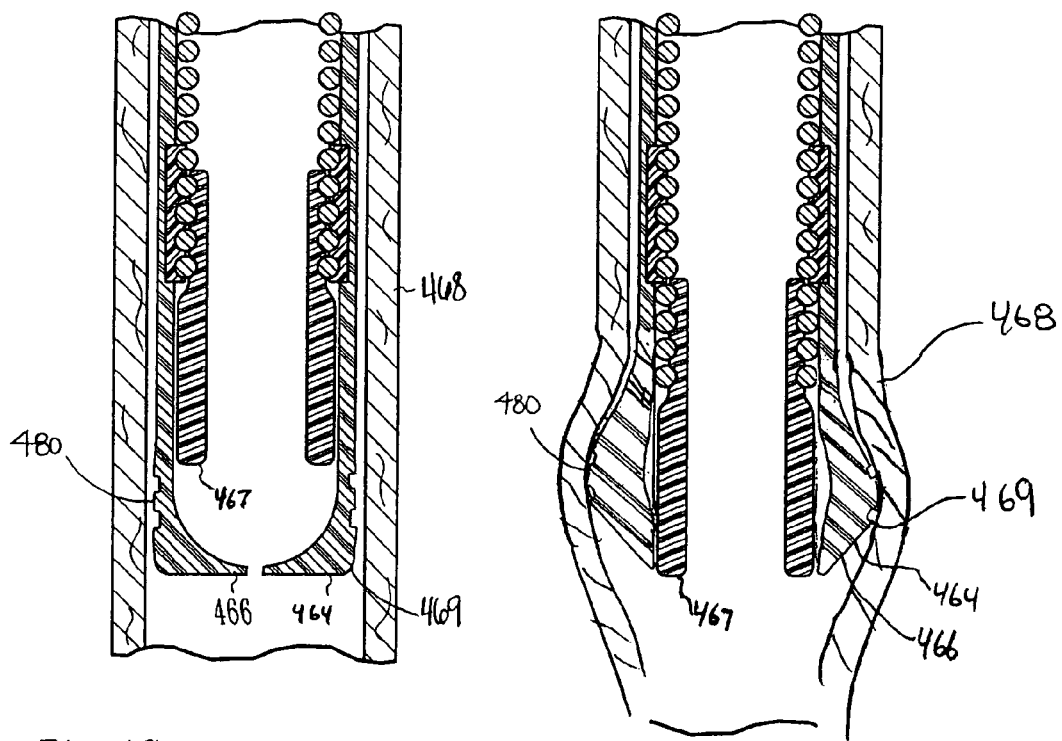
Fig. 4G
Fig. 4H

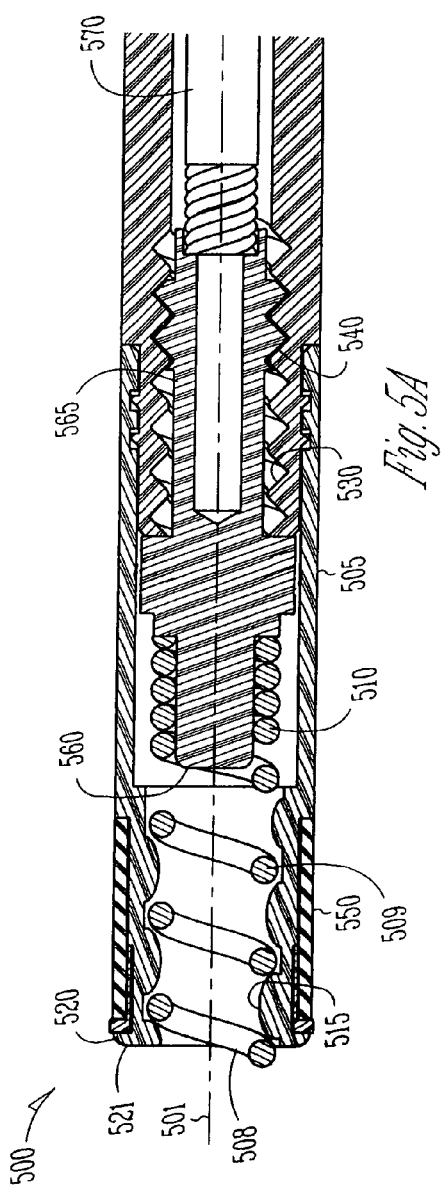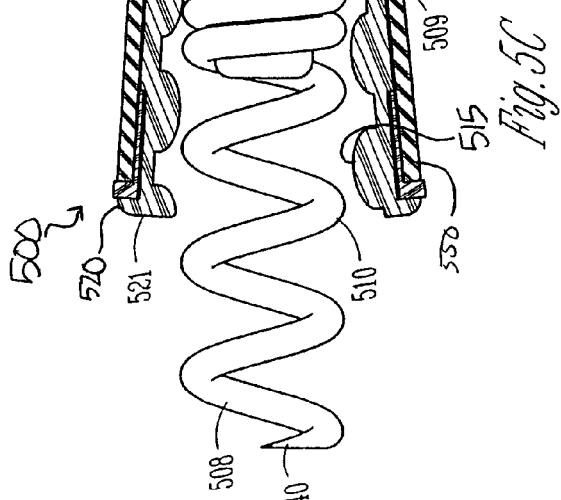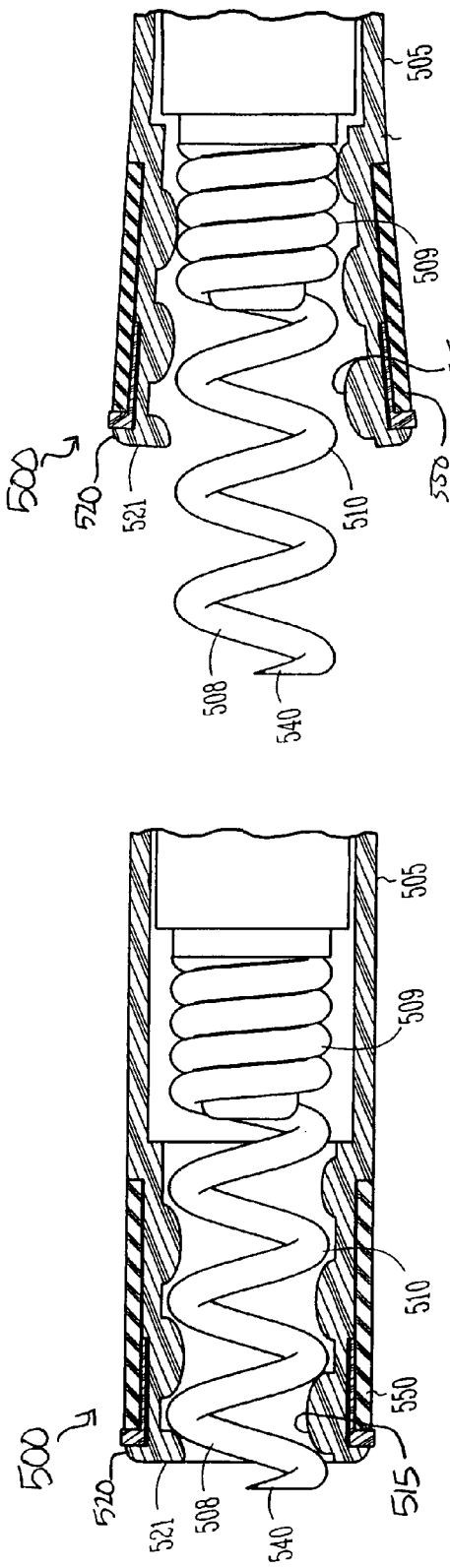

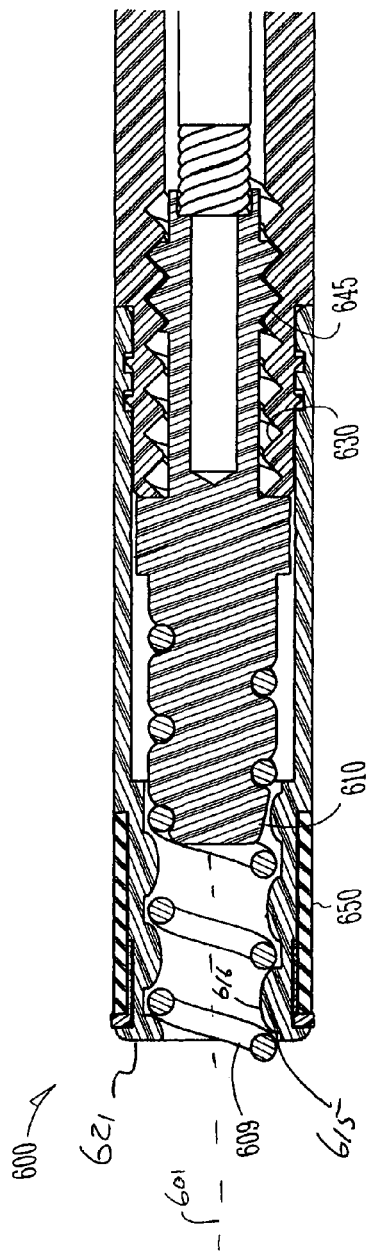
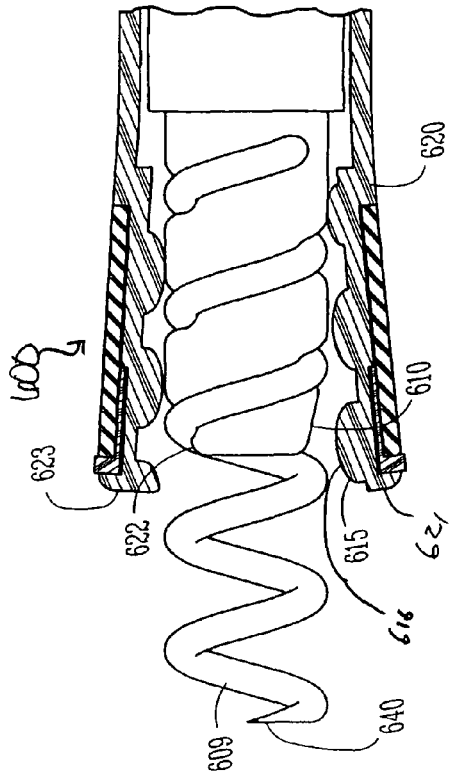
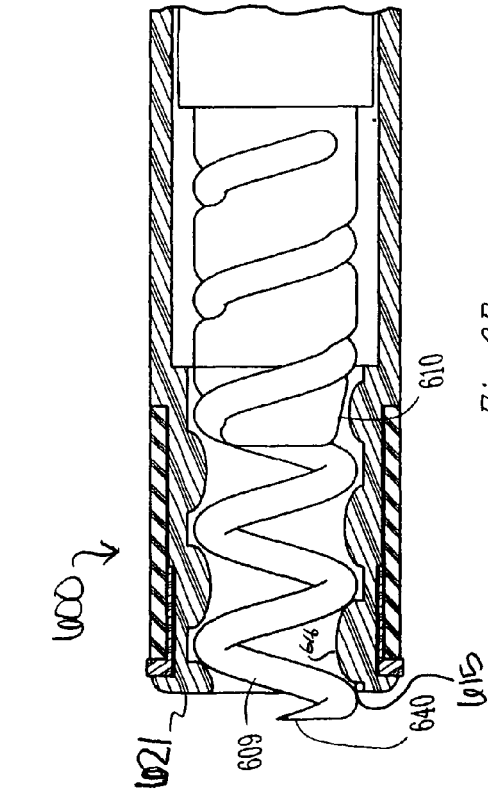

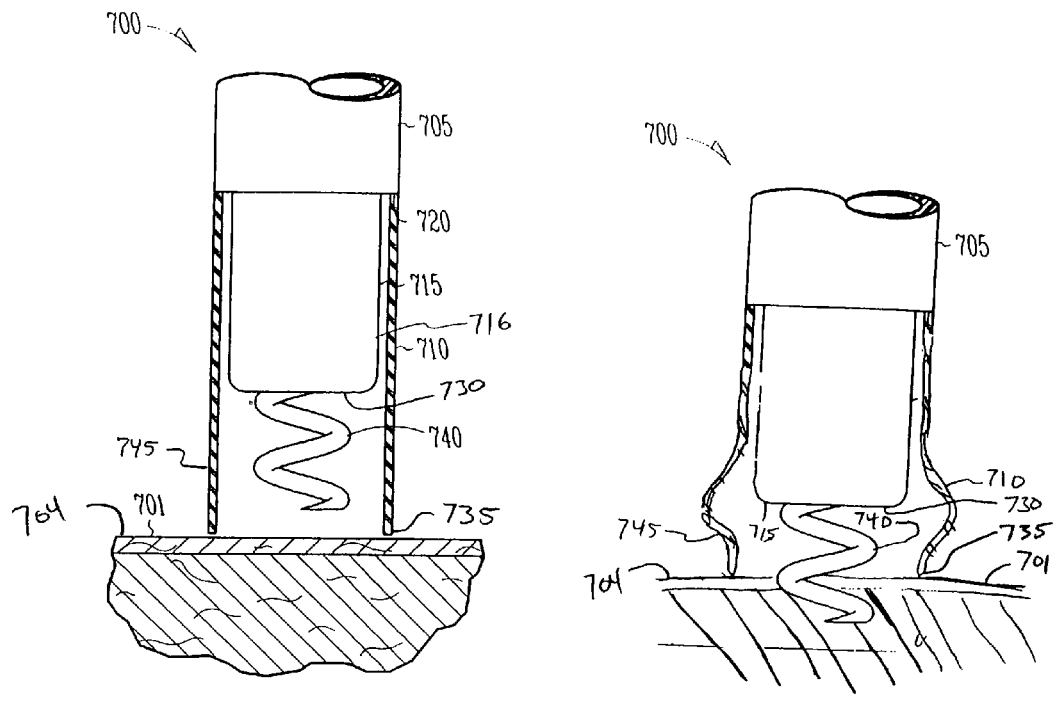
Fig. 7A
Fig. 7B
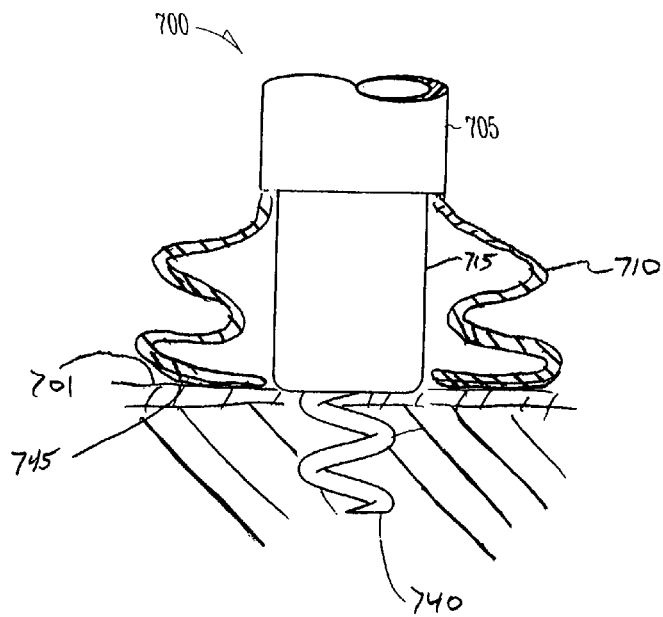
Fig. 7C

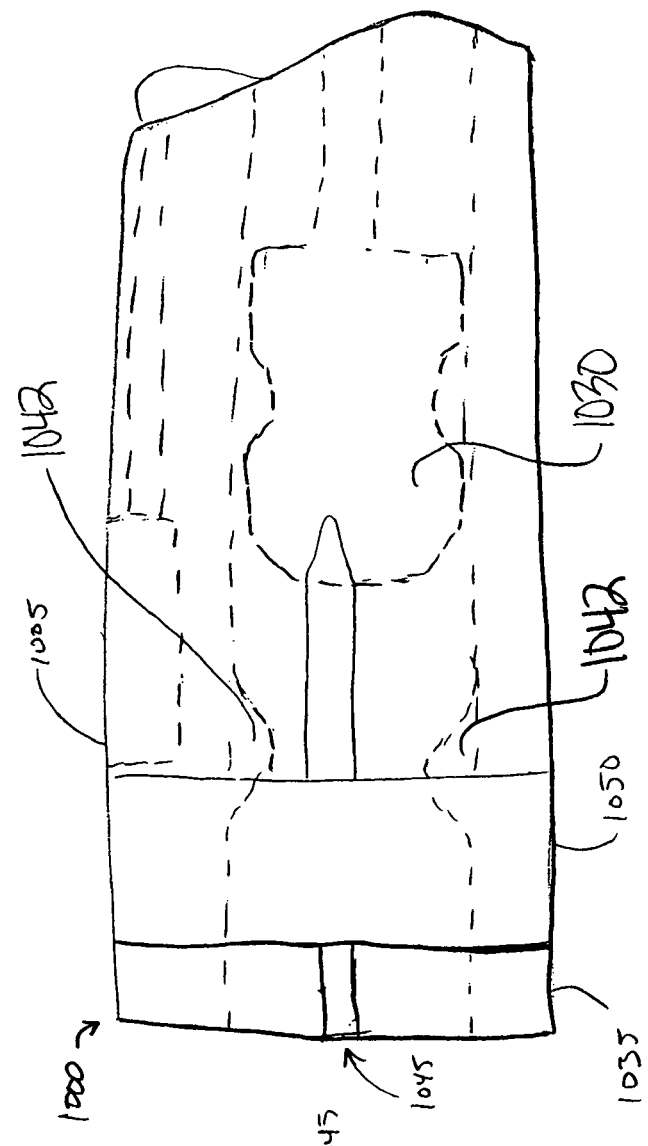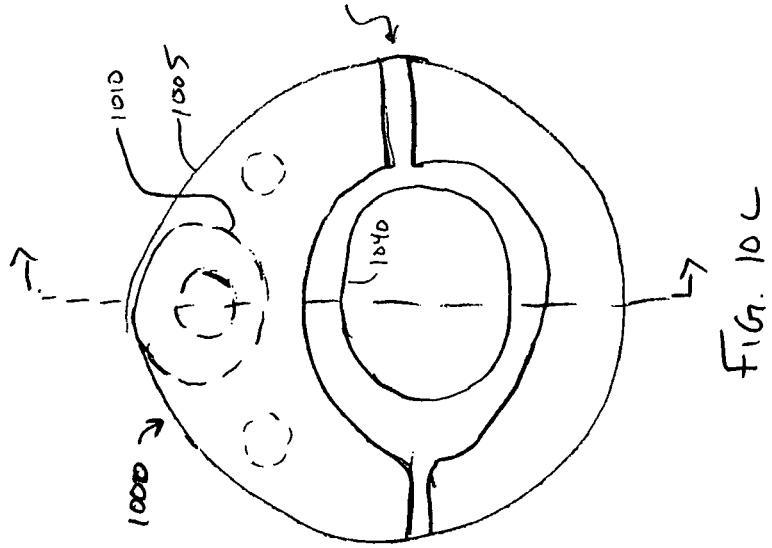

DEVICE ON LEAD TO PREVENT PERFORATION AND/OR FIXATE LEAD

TECHNICAL FIELD

This patent document pertains generally to medical device lead assemblies and more particularly, but not by way of limitation, to devices on lead assemblies to prevent perforation of a tissue wall or fixate a lead assembly in a vessel.

BACKGROUND

Medical devices such as pacers and defibrillators connect to one or more lead assemblies that carry an electrical signal to or from a location of the body. In some instances, a lead assembly is inserted into the heart and fixated in a heart wall. In some devices, a fixation structure, such as a barb or helix, is used to fix to a tissue surface. A fixation helix may be screwed into a heart wall, for example. When inserting a fixation structure such as a fixation helix into a tissue wall, it is desirable to avoid perforation of the wall with the lead body, i.e. to avoid creating an excessively thinned area or a hole in the tissue wall.

In other instances, a lead assembly is fixated in a vessel, such as a blood vessel. For example, a lead assembly may be fixed in a coronary vein to allow pacing, sensing or delivery of therapies. Lead assemblies may also be fixated in other blood vessels or other locations.

SUMMARY

An example lead assembly includes a lead body extending longitudinally along a lead axis, a driver axially displaceable relative to the lead body, and a driven member coupled to the lead body. The driven member is displaceable away from the lead axis and at least partially defines an expandable passage having at least one internal dimension. The driver is displaceable into the expandable passage and has at least one outer dimension that is larger than the at least one internal dimension of the expandable passage.

In another example, a lead assembly includes a lead body extending longitudinally along a lead axis, the lead body having a proximal end and a distal end, a fixation structure proximate the distal end of the lead body, a displaceable member coupled to the lead body and displaceable away from the lead axis, and a means for urging the displaceable member away from the lead axis. The displaceable member has an outer surface contactable against a tissue surface proximate the fixation helix.

In another example, a lead assembly includes a lead body extending longitudinally along a lead axis and having a lumen having at least one wall portion following a curved path, and a driver disposed in the lumen and displaceable into the portion of the lumen following the curved path. The lead body has first and second wall portions proximate the lumen. The first wall portion is thicker than the second wall portion. The lead body is changeable in shape when the driver is disposed into the portion of the lumen having a curved path.

An example method includes disposing a first member having a first cross-section in a lead assembly having a lead axis, an expandable passage, and a displaceable member proximate the expandable passage. The first member has at least one cross-sectional dimension larger than at least one corresponding cross-sectional dimension of the expandable passage. The example method further includes urging the first member into the expandable passage in the lead assembly, and urging the displaceable member away from the lead axis to expand the expandable passage.

BRIEF DESCRIPTION OF THE DRAWINGS

The drawings illustrate generally, by way of example, but not by way of limitation, various embodiments discussed in the present document.

FIG. 4A is a partial cross-sectional view of another example lead assembly.

FIG. 4B is a partial cross-sectional view of the lead assembly of FIG. 4A fixated in a blood vessel.

FIGS. 4C, 4D, and 4E are respective front, side, and back views of an example tooth.

FIG. 4F is an enlarged cross-sectional view showing an optional detent feature of a lead assembly.

FIG. 4G is an enlarged cross-sectional view showing an optional sealing configuration of a lead assembly.

FIG. 4H is an enlarged cross-sectional view showing a lead assembly having a tooth configuration engaged with a blood vessel.

FIG. 5A is a partial cross-sectional view of a lead assembly including a helical member.

FIG. 5B is a cut-away view showing a portion of the lead assembly of FIG. 5A, with the helical member in a withdrawn configuration.

FIG. 5C is a cut-away view showing a helical member in an extended configuration and a driven member displaced away from the lead axis.

FIG. 6A is a partial cross-sectional view of a lead assembly including a driver member disposed in a helical member.

FIG. 6B is a cut-away view showing a portion of the lead assembly of FIG. 6A, with a helical member and driver member in a withdrawn configuration.

FIG. 6C is a cut-away view showing the helical member and interference member in an extended configuration and a driven member displaced away from the lead axis.

FIG. 7A is a side view of a lead assembly having a sleeve, a lead body, and fixation structure engaging in a tissue wall.

FIG. 7B is a side view of the lead assembly of FIG. 7A that shows an end of the sleeve and lead body contacting a tissue wall surface.

FIG. 7C is a side view of the lead assembly of FIG. 7A that shows the sleeve buckling on the lead body.

FIG. 10C is an end view of the lead assembly of 10 A.

FIG. 10D is a side view of the lead assembly of 10A.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference.

A lead assembly includes an expanding and/or bending structure that fixates the lead in a vessel or prevents perforation of a tissue wall. A variety of example lead assembly structures and methods are shown and described in this application. FIGS. 1A-1B, 2D, and 4A-4H show portions of example lead assemblies that are expandable to fixate the lead assembly in a vessel, such as a coronary vein or artery. FIGS. 2A-2C, 3A-3C, 5A-5C, 6A-6C, and 7A-7C show portions of example lead assemblies that are expandable to prevent perforation of a distal tip of the lead assembly into a tissue wall. In an example, a portion of a lead assembly, such as a lead body, includes a passage that has an inner diameter that is smaller than an outer diameter of an internal component. In an example, an expandable portion of a lead assembly is isodiametric with a lead body during insertion of the lead through vasculature. In an example, electrodes and drug elution features are incorporated on, into, or near the driven member.

While many of the examples are shown either fixating a lead assembly in a vessel or preventing perforation in a tissue surface, the disclosed expanding structures can be adapted for use in fixation or perforation-prevention applications. For example, the structure shown in FIG. 1A-1B, while shown as lead fixation device, can also be adapted for prevention of perforation. The structures shown in FIGS. 2A-2C and 3A-3C, while shown as perforation-prevention devices, can also be adapted as fixation devices.

Figure 1A:
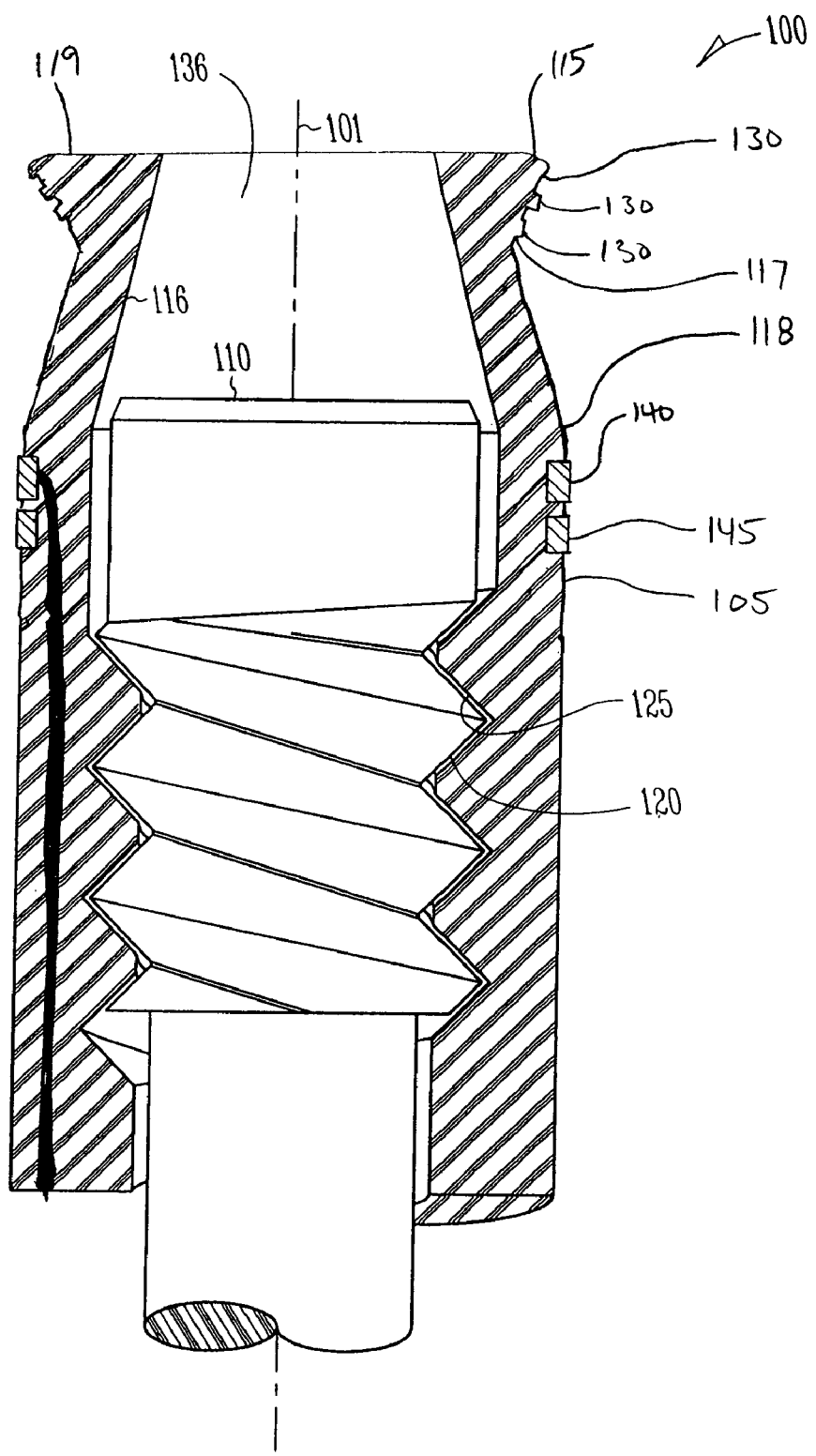
FIG. 1A is a partial cross-sectional view of an example lead assembly including a driver and a driven member displaceable away from a lead axis.

Referring now to FIG. 1A, a lead assembly 100 includes a lead body 105 defining a lead axis 101. The lead assembly 100 also includes a driver 110 and at least one displaceable member or driven member 115. In an example, the lead body 105 is a tubular structure formed from a soft polymer, such as silicone, or a more rigid polymer that is formable into a living hinge. In an example, the driver 110 and driven member 115 are machined, extruded, or molded. In an example, the driver 110 includes a piston. The driver 110 is axially displaceable relative to the lead body 105. In an example, the driver 110 and/or driven member are symmetrical around the lead axis 101. In another example, the driver and/or driven member are asymmetrical.

The driven member 115 is coupled to the lead body 105 and is optionally integral with the lead body. In an example, the driven member is displaceable away from the lead axis 101. In the example shown in FIGS. 1A-C, the driven member 115 is located near a distal end of the lead assembly. In alternative examples the driven member is located at other locations in the lead assembly. In an example, the driven member 115 is a portion of the lead body 105. Alternatively, the lead assembly includes a separate piece, such as an end cap, that includes the driven member 115.

Figure 1B:
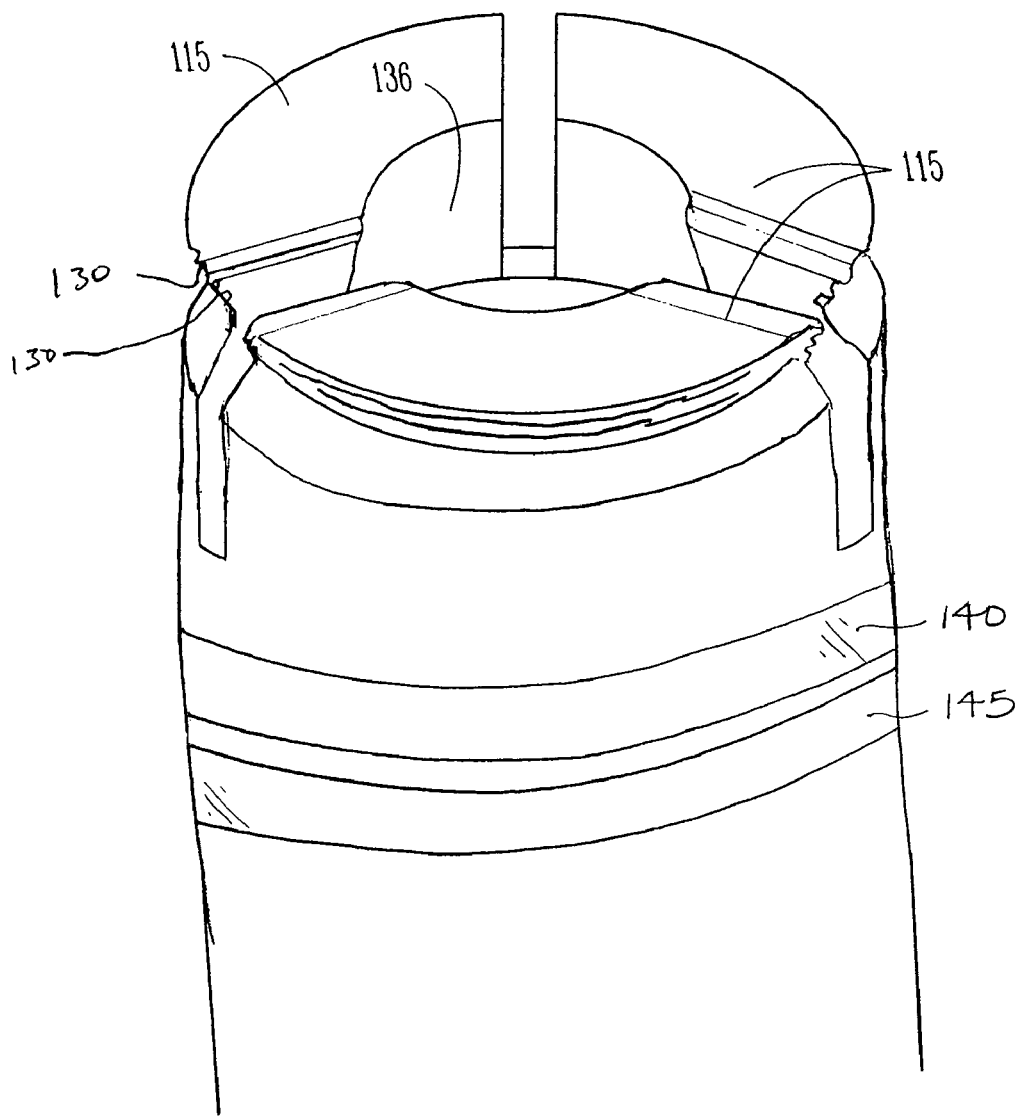
FIG. 1B is a perspective view of the example lead assembly shown in FIG. 1A.
Figure 1C:
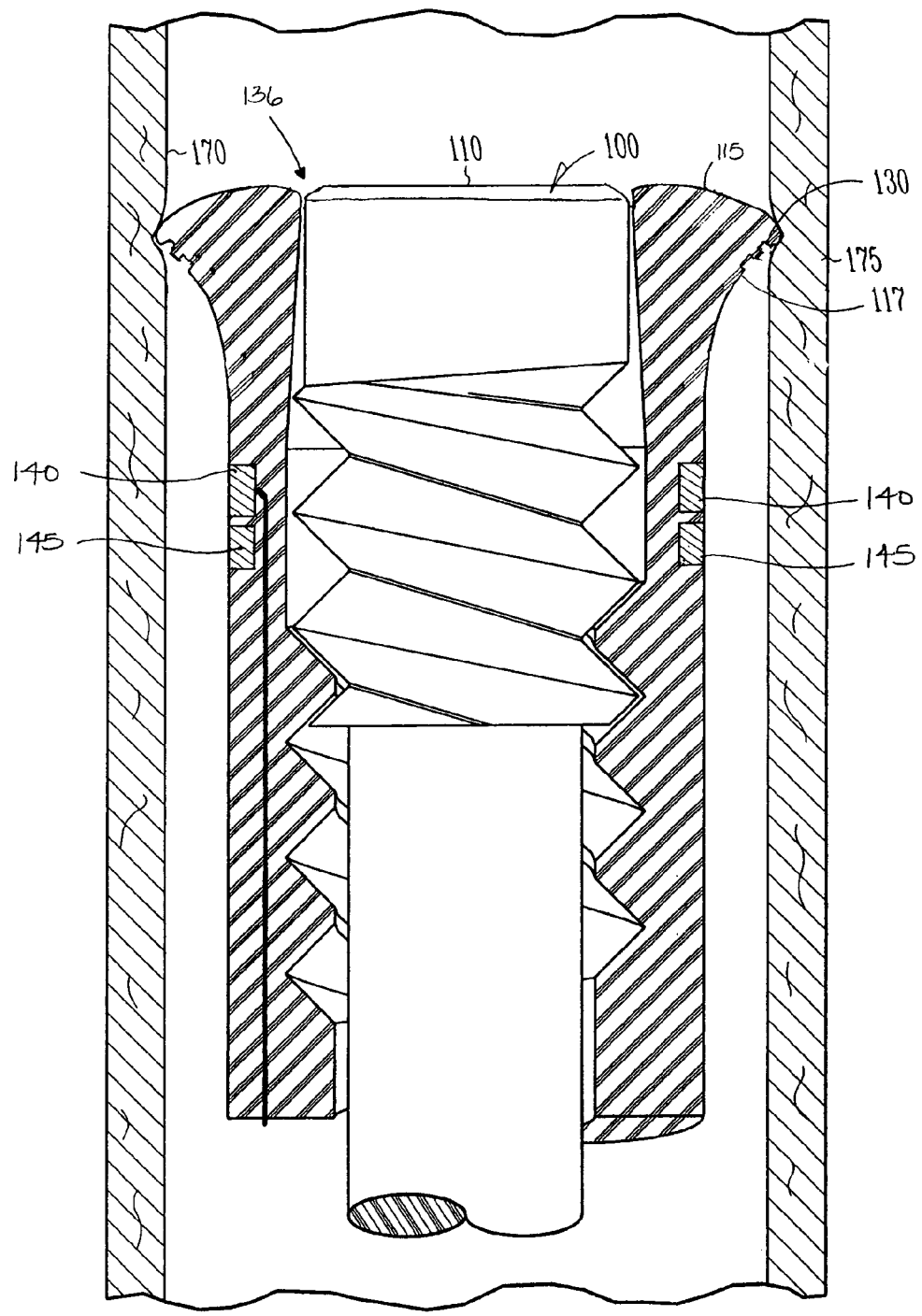
FIG. 1C is a partial cross-sectional view of the lead assembly shown in FIG. 1A fixated in a vessel.

Referring now to FIGS. 1A, 1B, and 1C, the lead assembly includes at least one passage 136 that is at least partially defined by the one or more driven members 115. FIG. 1B shows a perspective view of an example lead assembly configuration in which three driven members 115 define an internal passage 136. The driver 110 pushes outwardly on the one or more driven members 115 as it moves into or through the passage 136. In an example, the driver 110 has a diameter that is larger than a diameter of the passage 136. As shown in FIG. 1C, as the driver 110 is moved axially through the passage, the lead assembly expands, thereby increasing the lead diameter, and fixating the electrode in a blood vessel or other tubular organ.

Referring again to FIG. 1A, in an example, the driver 110 pushes against an inclined surface 116 of the driven member 115, which causes the driven member to rotate outwardly away from the lead axis 101. In an example, a portion 118 connecting the driven member 115 to the lead body is preferentially bendable and which allows the driven member to rotate outwardly. In an example, the portion 118 is weakened, thinned, or has altered of different material properties to enhance its bending properties. In an example, material is removed from the portion 118 to locally reduce the wall thickness and enhance bending properties. In an example, the portion 118 acts as a living hinge. In an example, the driven member 115 and the portion 118 that acts as a living hinge are both integral with the lead body.

The driver 110 is coupled to a drive system that moves the driver axially through the lead assembly. In an example, the driver is coupled to a threaded shaft 120 that engages on internal threads 125 on the lead assembly. Turning the shaft 120 with respect to the lead assembly moves the shaft 120 on the threads 125 to advance the driver 110. In an example, a terminal, stylet, guidewire, or other component in the lead body 105 is coupled to the driver.

In an example, the lead assembly is fixateable in a vessel, as shown in FIG. 1C, for example. An outer surface 117 of the driven member 115 engages an inner surface 170 of a blood vessel 175 or other tubular organ. One or more optional teeth 130 protrudes from the outer surface 117 to engage the inner surface 170 of the vessel. In an example, tooth 130 is a ridge that extends circumferentially around the surface 170. In an example, the tooth forms an acute angle which facilitates fixation. Alternatively, the edge of the tooth 130 is chamfered or rounded. In an example, the tooth has a high-friction surface that promotes fixation. In an example, the surface roughness of the tooth is increased. In another example a coating is applied to the tooth to increase the surface friction and/or roughness. In another example, features such as ridges are provided on the driven member to promote fixation.

Figure 1D:
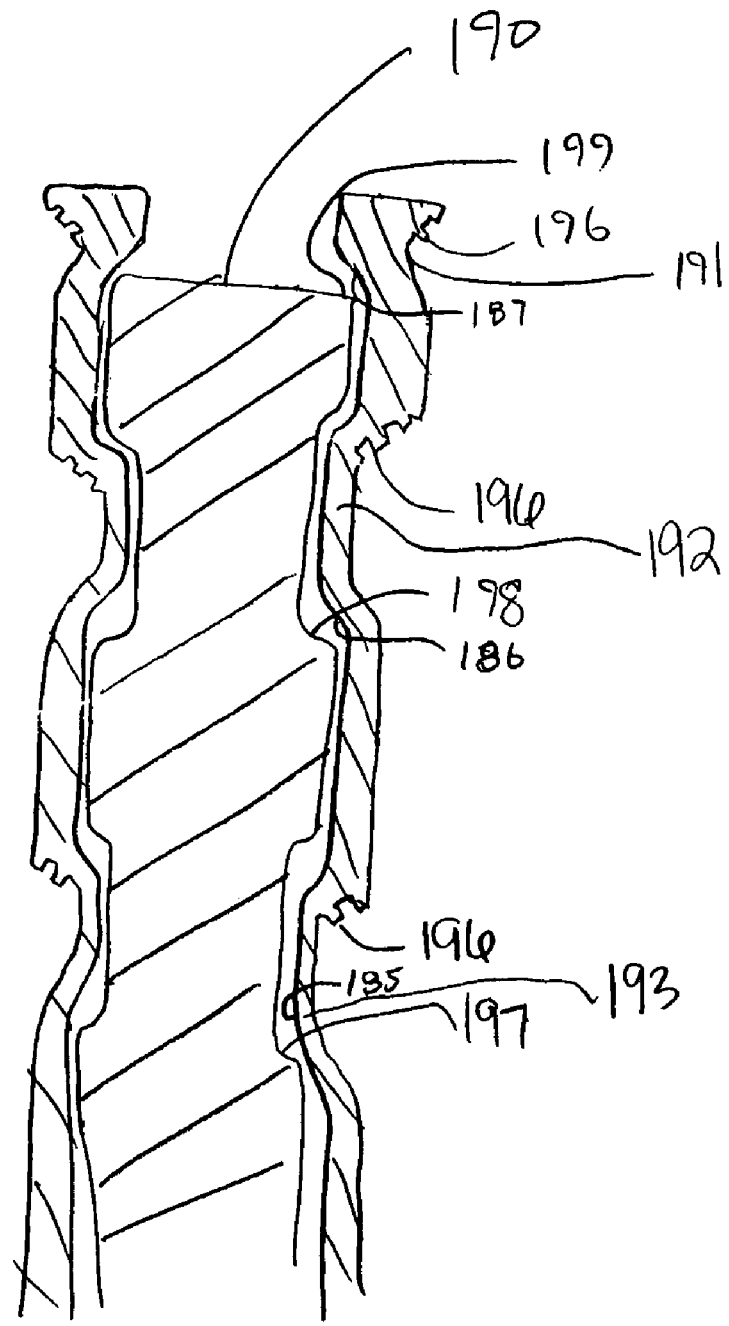
FIG. 1D is a cross-sectional illustration of a portion of a lead assembly including multiple driven members spaced axially on the lead assembly.

In an example, a driver engages multiple sets of driven members that define multiple passages at locations spaced axially along the length of the lead. For example, FIG. 1D shows a driver 190 and driven members 191, 192, 193 having teeth 196. Portions 197, 198, 199 of the driver 190 engage respective inner surfaces 185, 186, 187 of the driven members and push the driven members outward to engage a vessel.

In an example, an electrode 140 and/or drug collar 145 is provided on the driven member 115. FIG. 1A shows a drug collar 145 at the outer surface 117 of the driven member and electrode 140 embedded in the outer surface. In an example, the electrode 140 is connected to a conductor extending through the driven member 115. In an example, the location of an electrode 140 and/or drug collar 145 on the expandable member at the outer surface of the driven member 115 provides contact between the electrode and/or drug collar and a vessel in which the lead assembly is inserted.

In another example, the lead assembly is fixateable in a tissue wall, such as an internal wall of a ventricle or atrium. A fixation structure as a fixation helix can be attached to the driver 110 or integrated into the driver 110. The fixation helix shown in FIG. 2B, for example, can be attached to the driver 110 shown in FIG. 1A. A distal surface 119 on the driven member 110 is contactable against a tissue wall to prevent perforation of the wall as the fixation structure is engaged in the wall. In an example, the fixation helix is an electrode or includes an electrode.

Figure 2A:
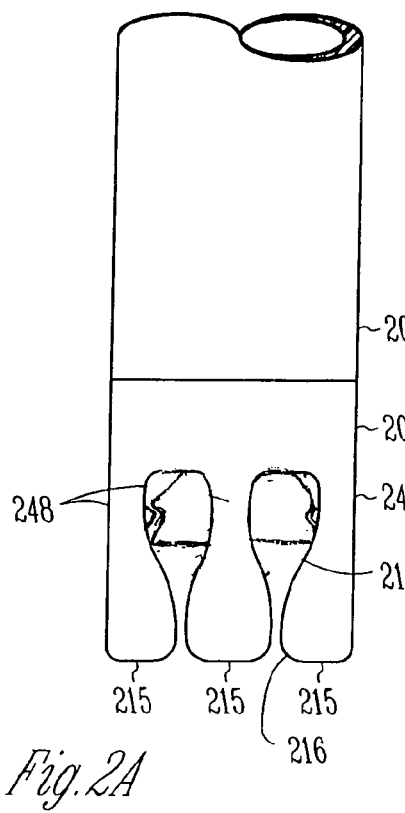
FIG. 2A is a partial side view of another example lead assembly.
Figure 2B:
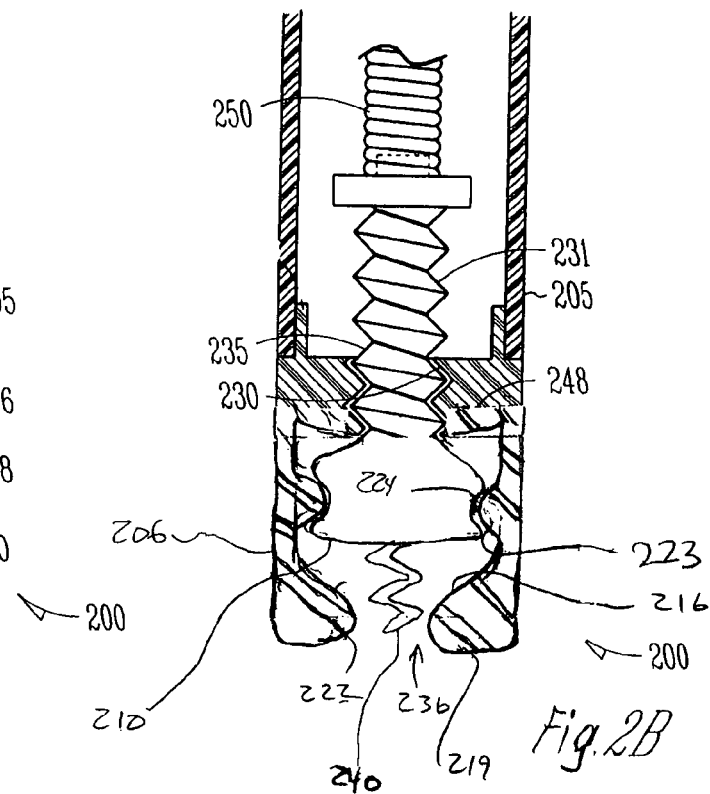
FIG. 2B is a cross-sectional view of the lead assembly shown in FIG. 2A.
Figure 2C:
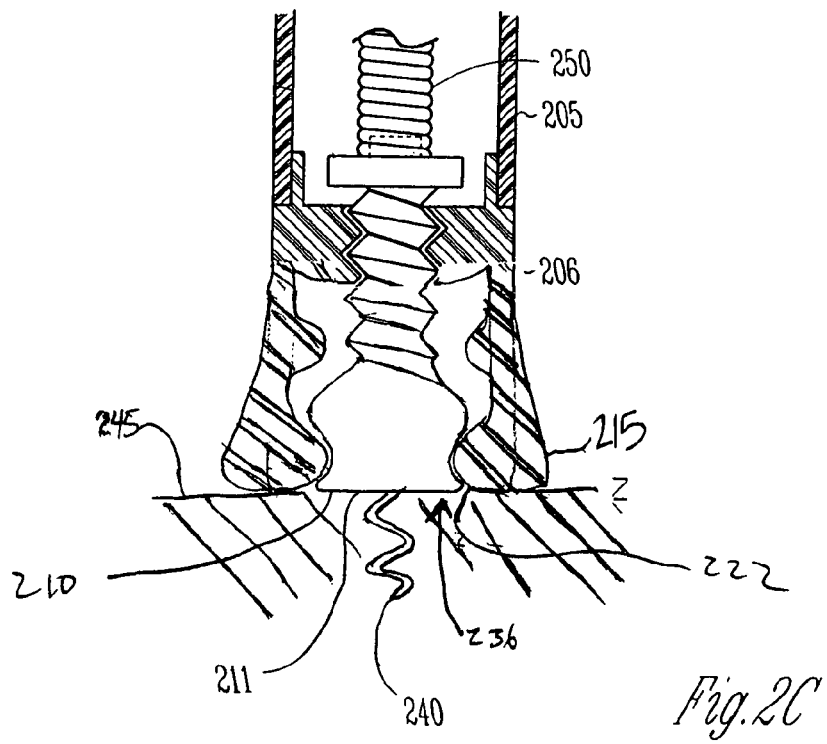
FIG. 2C is a cross-sectional view of the lead assembly of FIG. 2A that shows a fixation structure engaged in a tissue wall.

Referring now to FIGS. 2A-2C, another example lead assembly 200 includes a lead body 205, a driver 210, and a plurality of driven members 215 or displaceable members that are coupled to the lead body 205. The driver 210 is axially displaceable relative to the lead body 205 and driven members 215. In an example, an end piece 206 that includes the driven members 215 is coupled to the lead body 205. In alternative, the driven members 215 are integral with the lead body 205. In an example, each of the driven members 215 include a portion 248 that bends to allow displacement of the driven members. In another example, driven member 215 is coupled to the lead body with a hinge.

The driven members 215 define a passage 236. The driver 210 interferes with the driven members 215 to push the driven members outwardly. In an example, as the driver 210 is moved axially, the driver 210 contacts an internal face 216 on driven member 215. In an example, the driver has a circular cross-section that has a diameter that is larger than the diameter of the passage 236.

Referring now to the cross-section shown in FIG. 2B, in an example, the lead assembly includes a structure such as a detent that holds the driver 210 in a particular position with respect to the driven member or lead body. In an example, the driver 210 includes a concave structure 224 and one or more of the driven members includes a convex structure 223. The convex structure 223 engages the concave structure 224 to hold the driver in a retracted position. In an example, the concave structure is a groove extending around the driver 210. Referring now to FIG. 2C, when the driver 210 is sufficiently advanced through the passage 236, a second convex structure 222 of the driven member 215 engages the concave structure 224 on the driver. In an example, the second convex structure 222 and concave structure 224 operate as a detent to hold the driver in an extended position. In an example, the helix remains in the retracted position as the lead is inserted through vasculature or other anatomy and then is extended to fixate the lead assembly.

In an example, the lead assembly includes a threaded drive mechanism. FIG. 2B shows driver 210 includes connected to a threaded shaft 231 that includes external threads 235. The threads 235 engage on internal threads 230 on the end piece 206. Alternatively, the threads are coupled to or integral to the lead body 205. In an example, the threaded shaft 231 is coupled to a helical driver 250 that extends through the lead body 205. As used in this application, "helical" includes, but is not limited to, any coiled or spiral-shaped member, including members of varying radius or pitch, and is not intended to be limited to a structure with a constant angular dimension. In another example, the shaft is coupled to a stylet or guidewire.

Referring again to FIGS. 2B and 2C, a fixation structure 240 is coupled to the driver. In the example shown in FIGS. 2B and 2C, the fixation structure 240 includes a helix. In an example, the helix has a varying pitch and/or a varying diameter. In another example, the fixation structure includes a barb. As shown in FIG. 2C, the fixation structure 240 is engageable in a tissue wall 245, such as a heart wall. An end surface 211 of the driver contacts the tissue wall 245. An end surface 219 on the driven members 215 also contacts the tissue wall 245 and prevents perforation of the wall by the lead assembly. The spreading of the driven members 215 by the driver 210 increases the total surface area that contacts the tissue wall 245 to enhance resistance against tissue wall perforation. In contrast, if the driver 210 and passage 236 were configured to allow passage of the driver 210 without interference, the surface area that would touch the tissue wall 245 would be equal to or less than the cross-sectional profile of the lead assembly. Expanding the passage allows for a larger collective area on the driver 210 and lead assembly 205 to contact the tissue wall. For example, displacing the driven members away from the lead axis increases the profile of the lead assembly to increase the surface area that touches the wall and thereby decrease pressure (force per unit area) to increase the resistance to perforation of the wall.

Figure 2D:
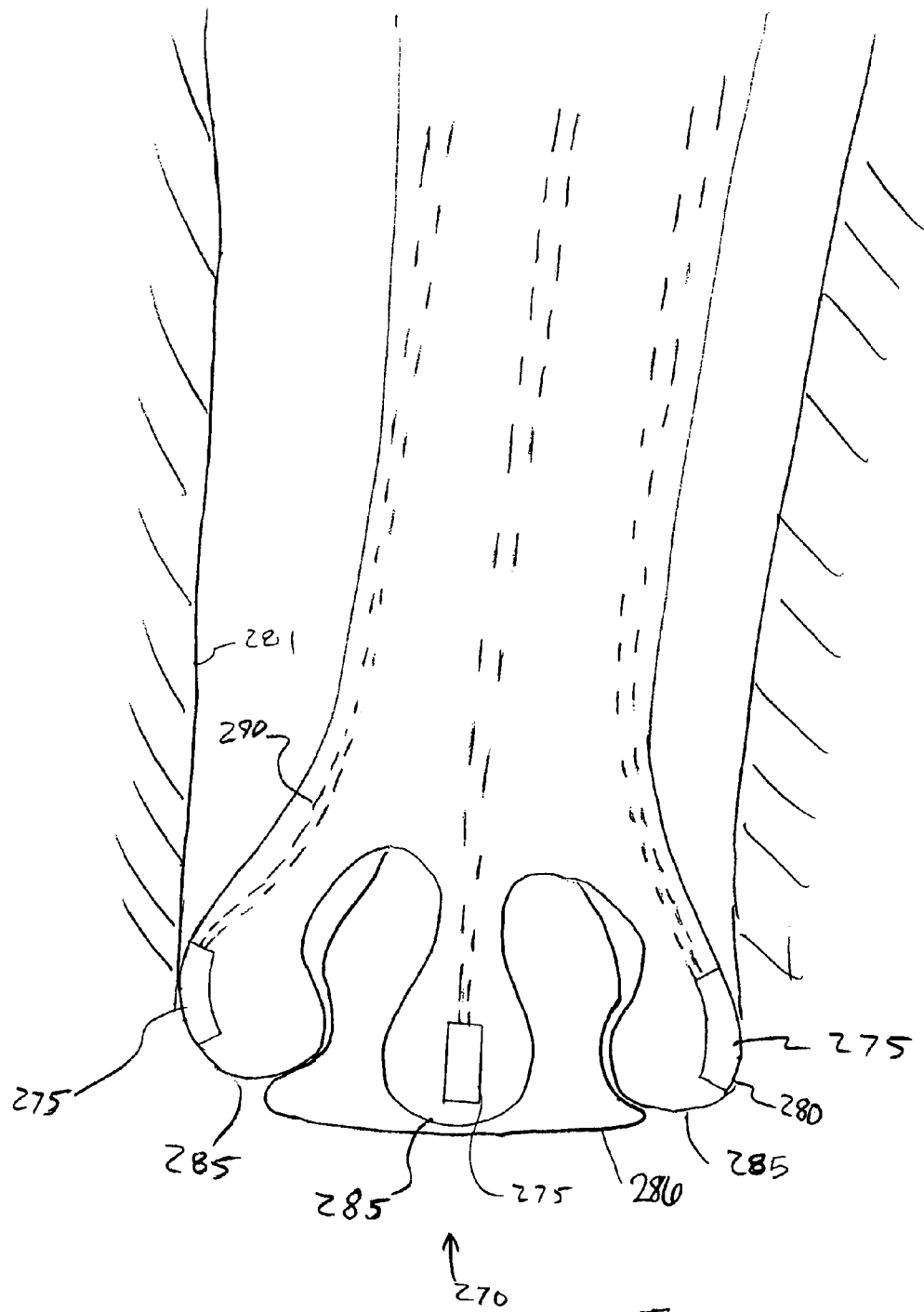
FIG. 2D is an illustration of a distal portion of a lead assembly contacting an internal surface of a vessel.
Figure 3A:
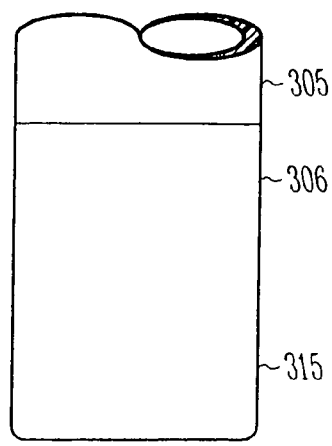
FIG. 3A is a side view of the lead assembly shown in FIG. 3A
Figure 3B:
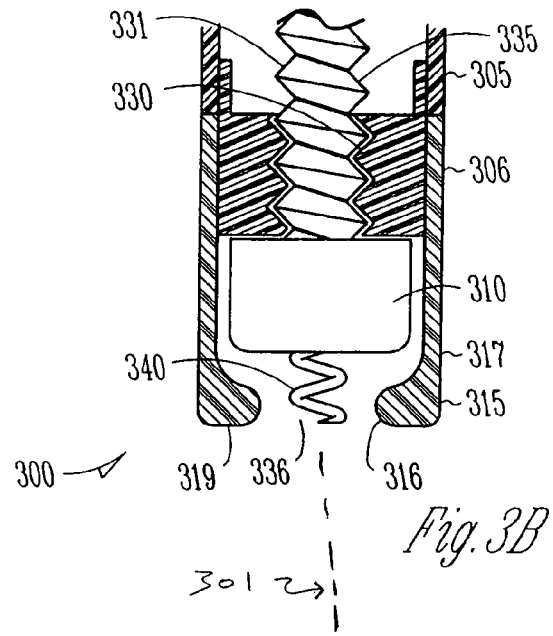
FIG. 3B is a partial cross-sectional view of another example lead assembly.
Figure 10A:
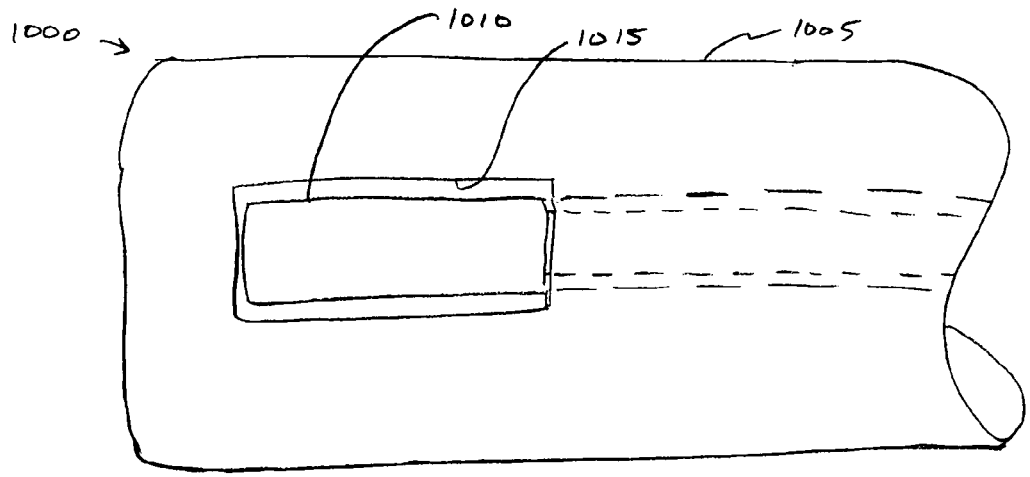
FIG. 10A is a top view of a portion of a lead assembly including an electrode.
Figure 10B:
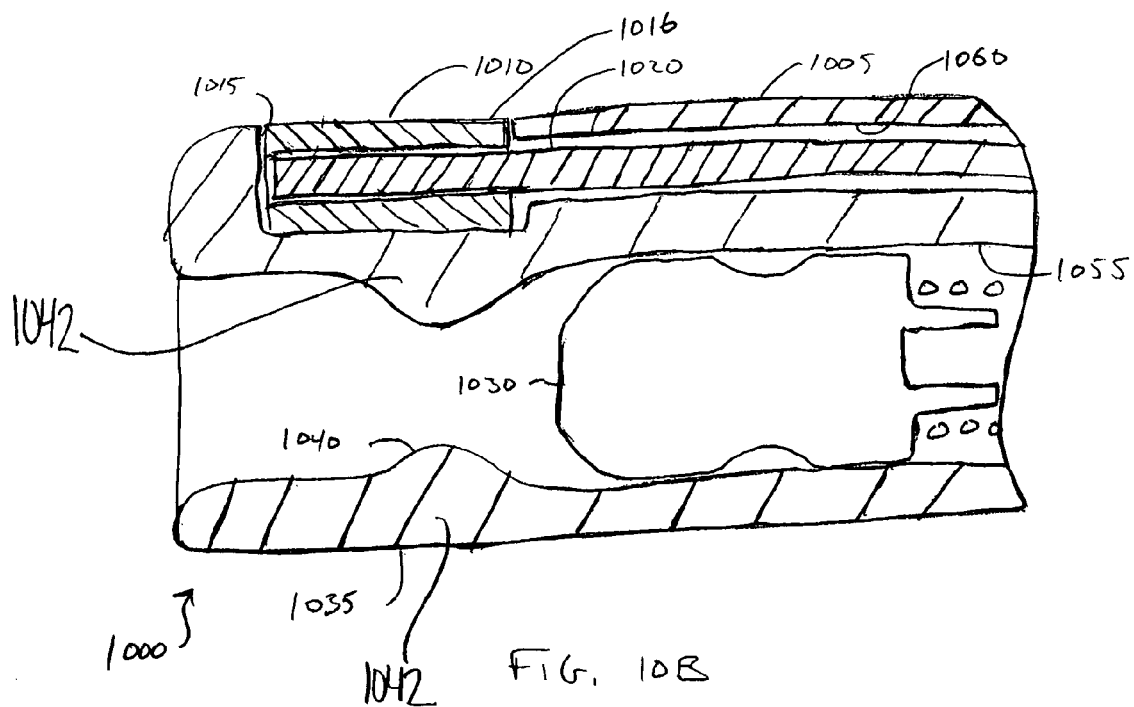
FIG. 10B is a cross-section side view of a portion of the lead assembly of FIG. 10A.

Alternatively, the lead assembly 200 shown in FIGS. 2A-2C is adapted for fixation in a vessel. FIG. 2D shows a portion of an example lead assembly 270 that is similar to lead assembly 200 but does not include a fixation helix. Driven members 285 are displaced outwardly by driver 286. An external surface 280 and/or an one or more optional electrodes 275 on the driven members 285 is engageable against in inner surface 281 of a blood vessel, such as a left ventricular vessel. In an example, one or more teeth, bumps, mesh, ridges, grooves, tines, electrodes, or drug collars are provided on the external surface 280. The optional electrodes 275 are coupled to respective conductors 290 such as insulated cables. In an example, the cables and electrodes are configured as shown in FIGS. 10A-10B. In an example, the electrodes are switchable, and a therapy is selectively deliverable through one electrode or a combination of electrodes, such as an electrode or electrodes that contact a myocardium and/or an electrode away from a phrenic nerve. In an example, selectively delivering a therapy to one or more electrodes allows for reduction in therapy energy and/or less phrenic nerve or diaphragmatic stimulation. In an example, the Referring now to FIGS. 3A-3D, another example lead assembly 300 includes an expandable driven member 315. In an example, some or all of the driven member 315 is formed from a stretchable or elastic material. FIG. 3A shows a side view of a lead body and end piece 306. FIG. 3B shows a cross-sectional view that shows a driver 310 that is displaceable with respect to the lead body 305 and contactable against an inner surface 316 of the driven member 315. In an example, the driven member 315 is an annular member that expands away from a lead axis 301 as the driver is pushed through a passage 336 defined by the annual member. In an example, the driven member 315 includes or is formed from an elastomer. In an example, an end piece 306 that is coupled to the lead body 305 includes the driven member 315. In another example, the driven member 315 is integral with the lead body 305.

In an example, the lead assembly 300 includes a threaded drive. The driver 310 includes or is connected to a threaded shaft 331 having external threads 335 that are engageable on internal threads 330 that are integral to or connected to the lead body 305. The threaded shaft 331 extends through the lead body, or is connected to another member such as a helical member that extends through the lead body.

Figure 3C:
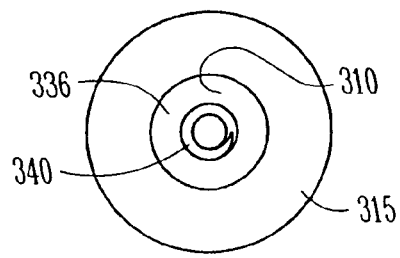
FIG. 3C is an end view of the lead assembly shown in FIG. 3A.
Figure 3D:
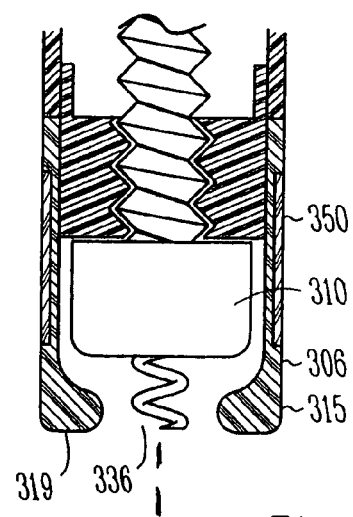
FIG. 3D is a partial cross-sectional view of a lead assembly including an optional stiffening structure.
Figure 5D:
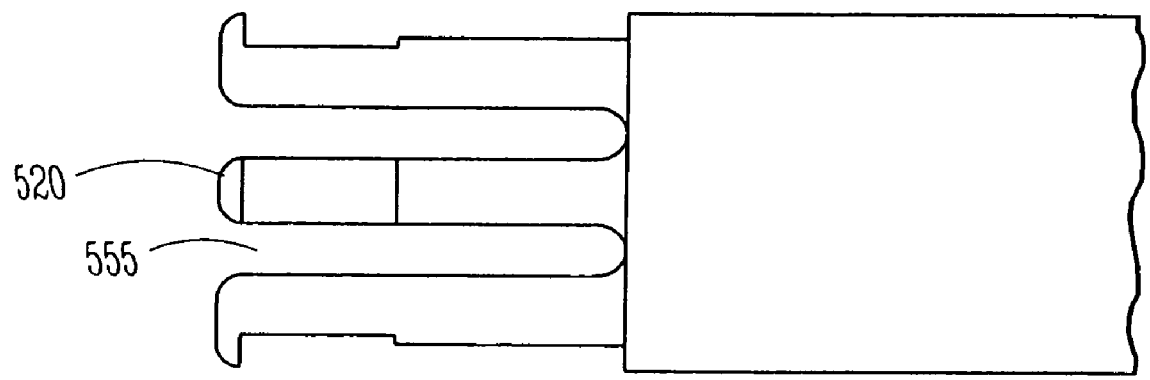
FIG. 5D is a side view of an end of a lead assembly that includes slots that accommodate radial expansion.

In an example, the lead assembly includes a fixation structure 340 engageable in a tissue wall. In an example, the fixation structure 340 is a fixation helix or a fixation barb. FIG. 3C is an end view that shows a fixation helix 340, passage 336, and driven member 315. An end surface 319 of the driven member 315 is contactable against the tissue wall engaged by the fixation structure 340 to resist perforation of the tissue wall by the lead assembly. The expansion of the drives members 315 increases the surface area that contacts the tissue wall to enhance the resistance against perforation of the wall. FIG. 3D is a cross-section that shows an optional member 350. In an example, the member 350 is a ring or coil that adds stiffness to the end piece 306. In an example, the member 350 is an elastic member that urges the driven members 315 when the driver 310 is withdrawn from the passage.

Alternatively, the lead assembly 300 shown in FIGS. 3A-3B is configured for fixation in a blood vessel. An outer surface 317 of the driven member 315 is engageable against an inner surface of a vessel. In an example, one or more teeth, electrodes, or drug collars are located in or on the outer surface.

Referring now to FIGS. 4A-4F, another example of a lead assembly 400, and portions thereof are shown. The lead assembly 400 includes a lead body 405, a threaded tube 440 having a helical inner structure 435 that engages a helical driver 430, and a tubular expander 410 coupled to the helical driver. The tubular expander 410 is a tube that extends inside the helical driver 430. Turning the helical driver 430 urges the driver, such as an expander 410 axially relative to a lead axis 401. The lead assembly also includes one or more driven members 415 that include an inner face 416 that is contacted by the expander 410 and pushed away from the lead axis 401. In an example, the one or more driven members 415 are integral with the lead body 405 and include a protrusion 419 that extends inwardly toward the lead axis 401. An outer surface 417 of the driven member 415 is contactable against an inner surface 403 of a vessel wall 404. In an example, contacting of the outer surface 417 of the driven member against the inner surface 403 of the vessel wall fixates the lead assembly in the vessel. In another example, the lead assembly includes a retractable tooth 450 that engages the vessel wall to fixate the lead assembly. FIGS. 4C, 4D, and 4E show a front view, side view, and back view respectively of the retractable tooth 450. In an example, the tooth includes a round end 451, a shaft 452, and a ring 456 extending around the shaft proximate an engagement end 453 of the retractable tooth. The tooth is disposed in an opening 454 in the driven member. As the expander 410 displaces the driven member 415 outwardly, the tooth 450 is pushed out of the opening to engage the inner surface 403 of the vessel wall 404.

FIG. 4F shows an enlarged view of a portion of the lead assembly and an optional detent feature. In an example, the expander 410 includes a concave portion 460 and the driven member 415 includes a convex portion 455 that is engageable in the concave portion of the driver to resist axial movement of the driver relative to the driven member. In an alternative configuration, the driven member includes a concave feature and the driver include a convex feature. In an example, the concave portion 460 and convex portion 455 are positioned so that the driven member 415 is in a displaced or expanded configuration when the convex portion engages the convex portion. This arrangement holds the lead assembly in a fixated position. Alternatively, the detent holds the assembly in another position, such as a non-expanded configuration.

FIGS. 4G and 4H show another example, in which the driven members 464 include inwardly-protruding portions 466 that optionally form a seal when the driver 467 is retracted. As shown in FIG. 4H, when the driver 467 is extended, it pushes the driven members 464 outwardly to fixate the lead in a vessel 468. In an example, an outer surface 469 of the driven member 464 includes one or more teeth 480 and/or a drug collar.

FIGS. 5A-5D show another example lead assembly 500 in which a driver is integrated with a fixation helix. The lead assembly 500, and portions thereof include a helical member 508 that includes a driver portion 510 and fixation helix portion 509 having a pitch that is different than the pitch of the driver portion. In some examples, the pitch and/or diameter of the driven portion and/or the fixation helix is variable. In the example shown in FIGS. 5A-5C, the fixation helix portion 509 has a larger pitch than the driver portion 510.

Referring again to FIGS. 5A-5C, in an example, the end of the lead assembly 500 includes an interference structure. In an example, the interference structure includes an internal helical structure 515. The fixation helix portion 509 of the helical member 508 fits within gaps defined by the helical structure 515. The driver portion 510 of the helical member 508 is designed to interfere with the helical structure to expand a portion of the lead assembly 500. In an example, the internal helical structure 515 is a separate component that is coupled to the lead body 505 or end piece 520. Alternatively, the internal helical structure is molded into the end piece 520 or otherwise integral with the end piece. As the helical member 508 is advanced through the lead body 505, the driver portion 510 of the helical member 508 interferes with the internal helical structure 515 and pushes the helical structure and connected components outwardly away from a lead axis 501. In an example, the internal helical structure has a decreasing inner diameter (I.D.) toward the distal end 521 of the lead assembly. In other words, the ridges or "threads" on the internal helical structure increase in height toward the end 521 of the lead assembly. The increasing height (or decreasing I.D.) of the internal helical member 515 provides for a progressive interference relationship between the driver portion 510 of the helical member 508 and the internal helical structure 515. As the driver is moved axially toward the distal end 521 of the lead assembly, there is a greater interference between the driver and the internal helical member 515, and the helical member and connected components are urged farther away from the lead axis. As the helical member engages into a tissue wall, the expanded end 521 of the lead assembly contacts the tissue wall to resist perforation of the wall.

In an example, the end of the lead assembly 500 is formed from an elastomer or soft polymer, such as silicone, that stretches to accommodate the expansion of the internal helical structure 515. In another example, the end 520 of the lead assembly is formed from a soft polymer and/or includes thinned wall sections that accommodate the expansion of the end of the lead assembly. In an example, the lead body is formed from a soft polymer and the end 520 of the lead assembly is integral with the lead body. In another example, shown in FIG. 5D, the end 520 of the lead assembly includes slots 555 that accommodate radial expansion of the end of the lead assembly. In an example, the slots extend axially. Alternatively, the slots extend helically.

Referring again to FIG. 5A-5C, in an example, the lead assembly includes a stiffening member 550 such as a ring or coil that extends around the lead body. In an example, the stiffening member 550 provides added axial stiffness to provide resistance against buckling of the end of the lead assembly. In another example, the stiffening member 550 urges or biases the end 520 of the lead assembly toward the lead axis to contract the end of the lead assembly when the driver portion 510 of the helical member 508 is withdrawn from the internal helical structure 515. In an example, the end of the lead assembly 500 is contracted during extraction of the lead assembly from the body.

In an example, the lead assembly 500 includes a threaded drive. In an example, a connector 560 extends inside the helical member 508 and includes or is connected to a threaded shaft 565. The threaded shaft 565 has threads 540 that engage internal threads 530 which are integral to or coupled to the lead body 505. Turning the shaft 565 on the threads advances the shaft and helical member 508 axially with respect to the lead body 505. In an example, a stylet 570 or other component is connected or coupled to the threaded shaft 565 and rotatable from an opposite end of the lead assembly 500.

Referring now to FIGS. 6A-6C, another example lead assembly 600 includes a helical member 609 that includes a fixation structure 640 such as a helix and an interference member, such as driver member 610 disposed within the fixation structure 640. The lead assembly 600 also includes a driven member 615 that includes or is coupled to an internal helical structure 616 that has a decreasing inside diameter (I.D.) towards the distal end of the lead. The helical member 609 fits within spaces defined by the internal helical structure 616. The driver member 610 progressively interferes with the helical structure 616 as the driver member 610 is moved axially. The progressive interference of the driver 610 with the internal helical structure 616 urges the driven member 615 outwardly away from the axis 601 of the lead. In an example, the driven member 615 includes elastomeric material, slots and/or thinned walls to accommodate radial expansion.

In an example, the driver 610 and the end 621 of the lead assembly include blunt end surfaces 622, 623. When the fixation structure 640 is engaged into a tissue wall, the blunt surfaces 622, 623 contact the tissue wall to prevent perforation of the wall by the lead assembly. In an example, the blunt surfaces 622, 623 are approximately perpendicular to the fixation structure 640. In an example, the lead assembly includes a threaded drive system 650 that includes an internally-threaded component 630 and a threaded shaft 645 that is coupled to the driver member 610.

Referring now to FIGS. 7A-7C, another example assembly 700 includes a sleeve 710 on the outside of the assembly that buckles and presses against a surface 701 of a tissue wall 704 to prevent perforation of the tissue wall. In an example, the sleeve 710 includes silicone rubber tubing. A fixation structure 740 such as a helix extends from an end 705 of the lead assembly 700. The sleeve 710 extends over a cylindrical surface 716 on an end component 715 of the lead assembly. The end 705 of the lead assembly 700 also includes a shoulder structure 720 that abuts the sleeve 710.

FIGS. 7A-7C illustrate the buckling of a sleeve as the fixation structure 740 is urged against the tissue surface 701. FIG. 7A, the lead assembly 700 is shown with a fixation structure 740 engaged in the tissue wall 704 and the sleeve 710 spaced from the tissue surface 701. FIG. 7A shows the end 735 of the sleeve 710 contacting the tissue surface 701. FIG. 7B shows the sleeve 710 beginning to buckle as the end 735 of the sleeve 710 is pushed against the tissue surface 701. In an example, sleeve 710 includes one or more features such as a groove, ring, ridge, male or female threads that control buckling of the sleeve. FIG. 7C shows an external surface 745 of the sleeve 710 pressing against the tissue surface 701 to prevent perforation of the tissue wall. In an example, the sleeve 710 expands to a diameter that is larger than the diameter of the end 730 of the end component 715 of the lead assembly 700 that is pushed against the tissue surface.

Figure 8:
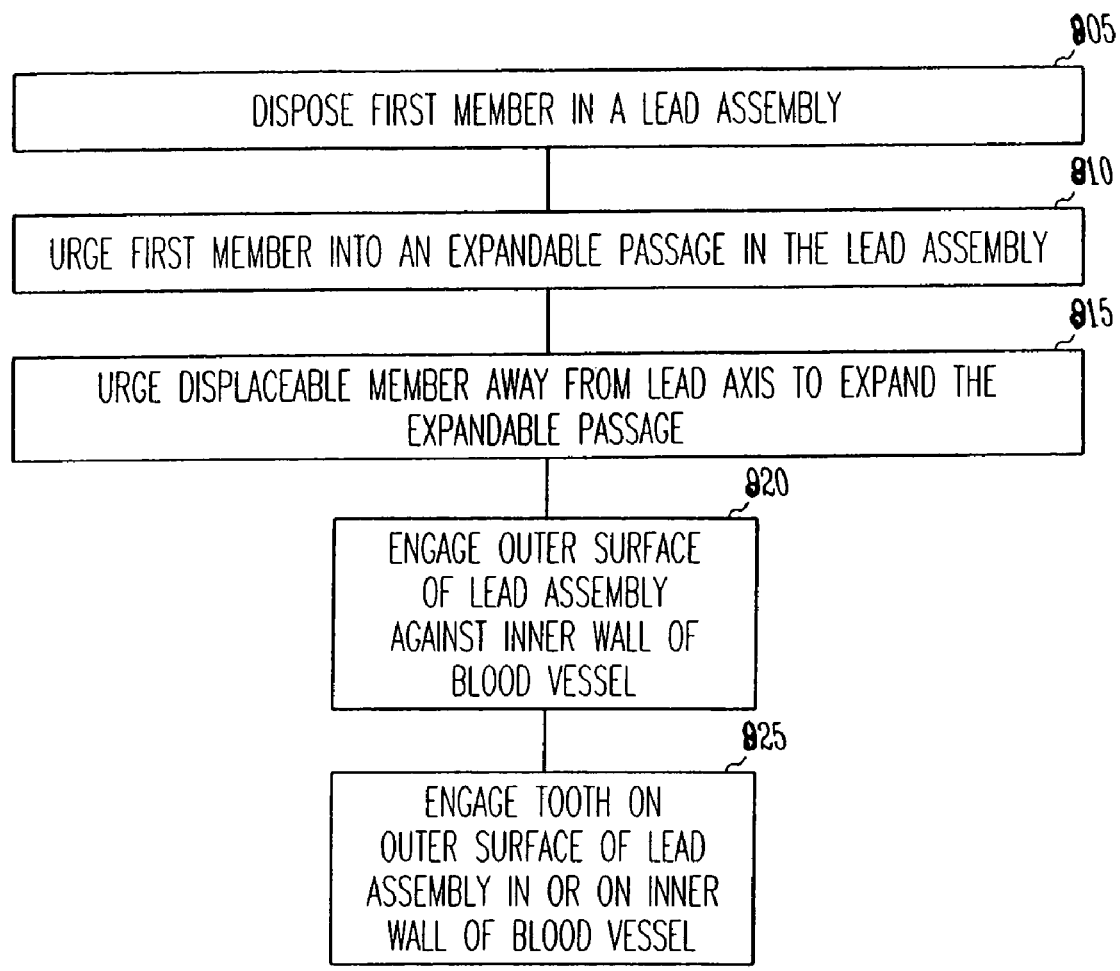
FIG. 8 is a flow chart that illustrates a method of using a lead assembly including an expandable passage.

FIG. 8 illustrates a method of fixating a lead assembly in a vessel or other tubular organ. At 805, a first member such as a driver is disposed in a lumen of a lead assembly. At 810, the first member is urged into an expandable passage in the lead assembly. At 815, a displaceable member is urged away from a lead axis to expand the expandable passage. In an example, the driver presses against the displaceable member as the driver is urged into the passage, thereby urging the displaceable member away from the lead axis and expanding the expandable passage. At 820, an outer surface of the lead assembly is engaged against an inner wall of a blood vessel. At 825, a tooth on the outer surface of the lead assembly is engaged in or on the inner wall of the blood vessel.

Figure 9:
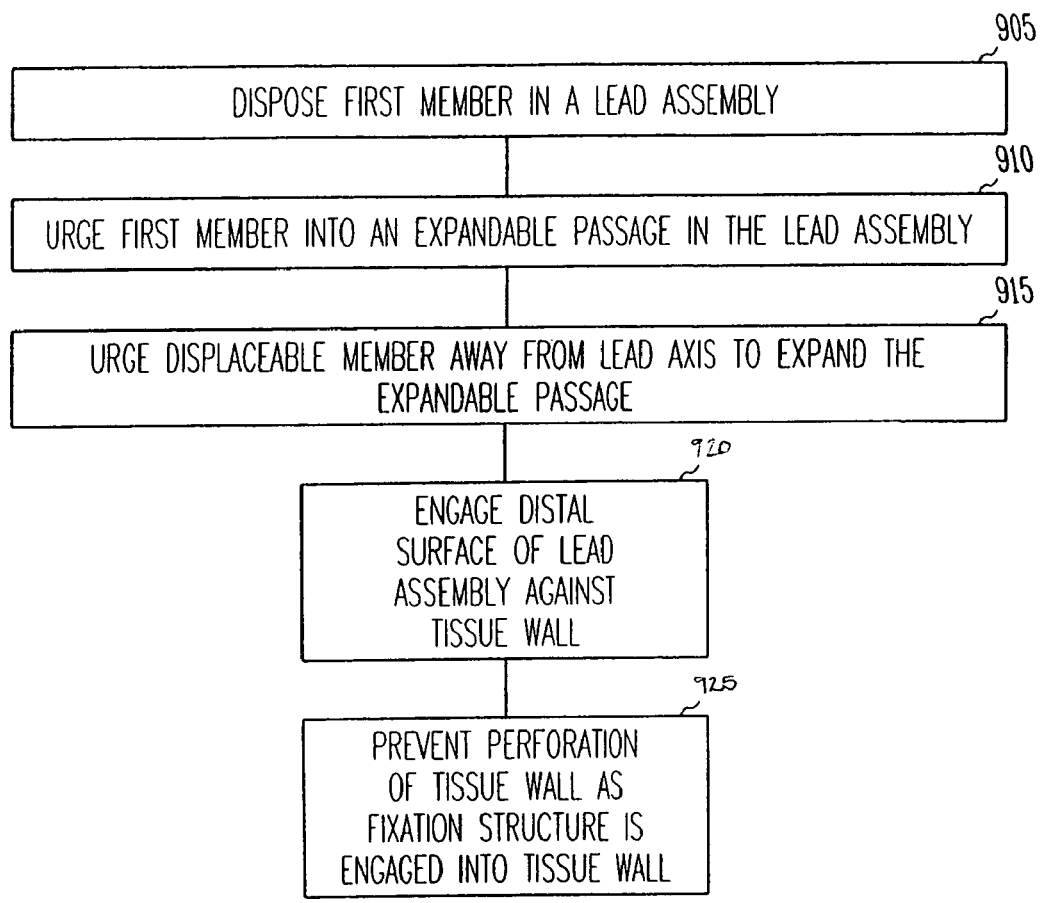
FIG. 9 is a flow chart that illustrates a method of using a lead assembly including to fixate a lead assembly on a tissue wall.

FIG. 9 illustrates a method of fixating a lead assembly. At 905, a first member such as a driver is disposed in a lumen of a lead assembly. At 910, the first member is urged into an expandable passage in the lead assembly. At 915, a displaceable member is urged away from a lead axis to expand the expandable passage. In an example, the driver presses against the displaceable member as the driver is urged into the passage, thereby urging the displaceable member away from the lead axis and expanding the expandable passage. At 920, an expanded distal surface on the lead assembly is engaged against a tissue wall. In an example, the distal surface is engaged on a ventricle wall. At 925, the expanded distal surface prevents perforation of the tissue wall as the fixation structure is engaged into the tissue wall. In an example, the expanded distal surface increases the surface area that contacts the tissue wall and reduces the pressure placed on the tissue wall.

Another example lead assembly is shown in FIG. 10A-D. FIG. 10A shows a top view of lead assembly 1000. FIGS. 10B, 10C, and 10D show a side cross-sectional view, end view, and side view respectively. Returning to FIG. 10A, the lead assembly 1000 includes a lead body 1005 that includes a hole 1015. In an example, the hole 1015 is punched or laser-ablated. An electrode 1010 is situated in the hole 1015. Referring now to the cross-sectional view in FIG. 10B, in an example, the electrode 1010 includes a tube 1016. A conductor 1020, such as a cable, extends through a lumen 1060 in the lead body 1005 and is electrically coupled to the electrode 1010. In an example, the conductor 1020 extends into the tube 1016. In an example, the tube 1016 is crimped onto the conductor 1020.

A driver 1030 is located in a second lumen 1055 in a tube. In an example, the second lumen 1055 is off-center to accommodate the electrode in the lead body. In an example, the driver 1030 pushes against an inwardly-extending portion 1040 of a distal portion 1035 of the lead assembly and urges a driven member 1042 outwardly. In an example, lead body 1005 includes the driven member 1042. Alternatively, the driven member 1042 is part of a separate component that is coupled to the lead body. In an example, the electrode 1010 is located on or in the driven member 1042. In an example, situating the electrode 1010 on the driven member 1042 promotes electrical contact with an inner surface of a blood vessel or other local anatomy. In an example, location of the electrode 1010 on a side of the lead assembly 1000 allows selective stimulation of a portion of a vessel. In an example, an electrical therapy or neural stimulation is delivered only to one side of a vessel. In an example, delivering an electrical therapy such as a pacing or antitachyarrhythmia therapy avoids stimulation of a phrenic nerve or diaphragmatic pacing.

Referring now to FIGS. 10C and 10D, in an example, the distal portion 1035 of the lead assembly includes a slit 1045 that allows the lead assembly to spread as the driver 1030 passes in inwardly-extending portion 1040. In an example, the lead assembly also includes a drug collar. In an example, the drug collar 1050 is elastic.

The electrode 1010 could alternatively be used in combination with one of the other lead assembly structures shown in FIG. 1A-C, 2A-C, 3A-D, 4A-H, 5A-D, 6A-C, 7A-D, or 8A-D. In an example, the electrode is situated in a laser-ablated or punched hole in one of the lead bodies shown in these figures.

The above specification, examples and data provide a complete description of the manufacture and use of the composition of the invention. Since many embodiments of the invention can be made without departing from the scope of the invention, the invention resides in the claims hereinafter appended.

What is claimed is:

1. A lead assembly configured for implantation within a blood vessel, the lead assembly comprising:
   a lead body defining a lead body lumen and extending longitudinally along a lead body axis with threads coupled to the lead body;
   at least one conductor extending within the lead body from a proximal end toward a distal end of the lead body;
   a driver disposed within the lead body lumen and axially displaceable relative to the lead body axis, the driver rotatable and axially displaceable on the threads; and
   a driven member integral with the lead body and displaceable away from the lead body axis, the driven member at least partially defining an expandable passage, the driver displaceable-from an opening into the expandable passage and through the expandable passage, the driver having at least one outer dimension that is larger than at least one internal dimension of the expandable passage, with the driven member including at least one weaker portion, the driven member to deform at the weaker portion to define an expanded exterior diameter that is larger than a non-expanded exterior diameter of the driven member when the at least one outer dimension of the driver is disposed in the expandable passage;
   wherein when the driven member defines the expanded exterior diameter, the driven member is configured to engage the vessel in order to fixate the lead assembly in the vessel while resisting perforation of the vessel by the lead assembly.

2. The lead assembly of claim 1, wherein the driven member is located at a distal end of the lead assembly.

3. The lead assembly of claim 2, further comprising a fixation helix connected to the driver and engageable into a tissue surface of a body.

4. The lead assembly of claim 3, wherein the driver includes a blunt surface proximate the fixation helix, at least a portion of the blunt surface on the driver contactable against the tissue surface.

5. The lead assembly of claim 4, wherein the driven member includes a blunt surface proximate the distal end of the lead assembly, at least a portion of the blunt surface contactable against the tissue surface.

6. The lead assembly of claim 1, wherein the driven member has a driver engagement surface inclined toward the lead axis and contactable against a surface on the driver.

7. The lead assembly of claim 6, comprising a bendable wall portion coupled to the driven member.

8. The lead assembly of claim 6, wherein the driven member includes an inwardly-extending protrusion including the driver engagement surface, the protrusion sealing the expandable passage.

9. The lead assembly of claim 1, wherein the lead assembly includes a vessel wall engagement surface engageable against an inner wall of the blood vessel, the vessel wall engagement surface outwardly displaceable by the driver.

10. The lead assembly of claim 9, wherein the lead body includes a cavity, the driver disposed in the cavity, the driven member integral with the lead body proximate the cavity and including the vessel wall engagement surface.

11. The lead assembly of claim 9, wherein the lead assembly further comprises at least one tooth engageable against the inner wall of the blood vessel.

12. The lead assembly of claim 11, wherein the lead body includes a compressible material proximate the tooth, the tooth disposed in the compressible material and at least partially retracted into the lead body when the compressible material is not compressed, and the tooth at least partially extended from the lead body when the compressible material is compressed.

13. The lead assembly of claim 1, further comprising helical internal threads coupled to the lead body, the driver including a helical member engageable on the threads and a pusher displaceable into the expandable passage.

14. The lead assembly of claim 1, wherein the driver includes a structure engageable with a portion of the driven member, the driver fixateable in a particular position with respect to the driven member by engagement of the structure with the portion of the driven member.

15. The lead assembly of claim 1, comprising a plurality of driven members contactable by the driver and displaceable away from the lead axis, each of the plurality of driven members including an engagement surface inclined toward the lead axis and slidable against the driver.

16. The lead assembly of claim 1, further comprising a conductor extending through a lumen in the lead body and an electrode electrically coupled to the conductor and situated proximate the driven member.

17. The lead assembly of claim 1, wherein the threads are disposed along an interior of the lead body.

18. A lead assembly for implantation within a blood vessel, the lead assembly comprising:
   a lead body defining a lumen and extending longitudinally along a lead body axis from a proximal end to a distal end;
   a conductor extending within the lead body from the proximal end in a direction toward the distal end of the lead body;
   a displaceable member integral with the lead body and displaceable away from the lead body axis, the displaceable member at least partially defining an expandable passage with the displaceable member including at least one weaker portion;

a means for urging the displaceable member away from the lead body axis, the means for urging displaceable from an opening into the expandable passage and through the expandable passage, the means for urging having at least one outer dimension that is larger than at least one internal dimension of the expandable passage, the displaceable member to deform at the weaker portion to define an expanded exterior diameter that is larger than a non-expanded exterior diameter of the displaceable member when the at least one outer dimension of the means for urging is disposed in the expandable passage; and a fixation structure coupled to the means for urging disposed proximate the distal end of the lead body, with the displaceable member having an outer surface to contact a tissue surface proximate the fixation structure, wherein when the displaceable member defines the expanded exterior diameter, the displaceable member is configured to engage the tissue surface in order to fixate the lead assembly to the tissue surface while resisting perforation of the tissue surface by the lead assembly.

19. The lead assembly of claim 18, wherein the lead assembly includes a stretchable tube, the displaceable member including a portion of the stretchable tube, the means for urging the displaceable member away from the lead axis configured to expand at least a portion of the stretchable tube away from the lead axis.

20. The lead assembly of claim 19, wherein the stretchable tube includes a portion having a first wall and a second wall that is thicker than the first wall, the displaceable member including at least a portion of the second wall.

21. The lead assembly of claim 18, wherein the displaceable member includes a protrusion that extends toward the lead axis, and the means for urging the displaceable member away from the lead axis is configured to push against the protrusion.

22. The lead assembly of claim 21, wherein the means for urging the displaceable member away from the lead axis further includes threads coupled to the lead body, a driver engageable on the threads, and a pusher coupled to the driver and contactable against the protrusion, wherein turning the driver on the threads moves the driver and pusher axially relative to the lead body to urge the pusher against the protrusion.

23. The lead assembly of claim 18, wherein the means for urging the displaceable member away from the lead axis includes threads connected to the lead body and a helical member engageable on the threads.

24. The lead assembly of claim 23, further comprising a tube coupled to the helical member, a portion of the tube extending from a distal end of the helical member and contacting the displaceable member.

25. The lead assembly of claim 23, wherein the helical member includes a first helical portion defining a gap between adjacent turns of the helical member, the means for urging the displaceable member away from the lead axis further comprising an interference member that extends through a portion of the gap between turns of the helical member and interferes with the threads.

26. The lead assembly of claim 23, wherein the helical member includes a first portion engageable on the threads and a second portion configured to interfere with the threads to urge the displaceable member away from the lead axis.

27. The lead assembly of claim 26, wherein the first portion has a first pitch and the second portion has a second pitch smaller than the first pitch.

28. The lead assembly of claim 18, wherein the displaceable member includes a flexible sleeve proximate the fixation structure and the means for urging the displaceable member away from the lead axis includes a means for folding the sleeve outwardly away from the lead axis, an outer surface of the sleeve contactable against the tissue wall to prevent perforation of the wall by the lead assembly.

29. The lead assembly of claim 28, wherein the sleeve includes a first end abutted against the lead body and a second end abuttable against the tissue wall.

30. A method for expanding a driven member of a lead assembly, comprising:

disposing a driver axially into a lumen of a tubular lead body of the lead assembly along a lead body axis, the lead body including a conductor extending within the lead body from a proximal end in a direction toward a distal end;

disposing the driver along threads of the lead body and into an internal passage of driven member integral with the lead body and expanding the driven member away from the lead body axis, with expanding the driven member including:

deforming the driven member at a weaker portion of the driven member by disposing the driver into the expandable passage, with an outer dimension of the driver being disposed into a portion of the expandable passage including an internal passage dimension smaller than the outer dimension; and expanding an exterior diameter of the driven member to a dimension larger than a non-expanded exterior diameter of the driven member, such that the driven member engages a blood vessel in order to fixate the lead assembly in the vessel while resisting perforation of the vessel by the lead assembly.

31. The method of claim 30, wherein the lead assembly includes a plurality of displaceable members and disposing the driver into the expandable passage includes disposing the driver against the plurality of displaceable members, wherein the plurality of displaceable members are displaced away from the lead axis.

32. The method of claim 31, further comprising engaging an outer surface of the lead assembly proximate the displaceable member against an inner wall of the blood vessel.

33. The method of claim 32, further comprising engaging a tooth on the outer surface of the lead assembly on the inner wall of the blood vessel.

34. The method of claim 30, wherein a fixation helix is coupled to the driver, the method further comprising engaging the fixation helix into a tissue wall and contacting the driver and displaceable member against the tissue wall.

35. The method of claim 34, wherein the fixation helix has a pitch and the lead assembly includes an internal helical protrusion having approximately the same pitch as the fixation helix, the at least one corresponding cross-sectional dimension of the expandable passage including an inner diameter of the internal helical protrusion, the fixation helix disposable in a gap defined by the internal helical protrusion, and the disposing the displaceable member away from the lead axis including urging the driver against the internal helical protrusion.

36. The method claim 30, wherein disposing the driver along threads includes driving a helix shaped fixation mechanism into an anchor location.

37. The method of claim 30, wherein the lead assembly includes internal threads and a portion of the driver includes external threads, wherein the disposing the driver into the expandable passage includes advancing the driver on the internal threads.

38. The method of claim 30, wherein a tooth is at least partially embedded in an outer surface of the lead assembly, and the disposing the driven member away from the lead axis pushes a portion of the tooth out of the lead assembly.

* * * * *